United States Patent [19]

Kisfaludy et al.

[11] 3,953,415
[45] Apr. 27, 1976

[54] PROCESS FOR THE PREPARATION OF BIOLOGICALLY ACTIVE POLYPEPTIDES CONTAINING ASPARTYL GROUP

[75] Inventors: Lajos Kisfaludy; Miklos Low; Istvan Schon; Tamas Szirtes; Maria Sz. Sarkozi; Sandor Bajusz; Andrae Turan; Rosa Beks; Attila Juhasz; Laszlo Graf; Kalman Medzihradszky; Laszlo Szporny, all of Budapest, Hungary

[73] Assignee: Richter Gedeon Vegyeszeti Gyar Rt, Budapest, Hungary

[22] Filed: May 14, 1973

[21] Appl. No.: 360,198

[30] Foreign Application Priority Data
May 15, 1972 Hungary.................................. 7776

[52] U.S. Cl.......................................... 260/112.5 R
[51] Int. Cl.². .................. C07C 103/52; C07G 7/00
[58] Field of Search................................ 260/112.5

[56] References Cited
UNITED STATES PATENTS
3,479,333   11/1969   Greven ........................... 260/112.5

OTHER PUBLICATIONS
Shibnev et al., Chem. Abstr. 68, 13374d, (1968).
Kisfaludy et al., J. Org. Chem., 35, 3563–3565, (1970).
Kovacs et al., J. Am. Chem. Soc., 89, 183–184, (1967).
Kisfaludy et al., Chem. Abstr. 68, 87559q, (1968).
E. Schroder and K. Lubke, "The Peptides," Vol. II, Academic Press, New York, (1966), pp. 214–215.

*Primary Examiner*—Lewis Gotts
*Assistant Examiner*—Reginald J. Suyat
*Attorney, Agent, or Firm*—Karl F. Ross; Herbert Dubno

[57] ABSTRACT

The invention relates to the preparation of biologically active polypeptides containing the aspartyl group, particularly an aspartyl-glycine moiety, using the active-ester technique.

According to the method of the invention, human adrenocorticotropic hormone and its fragments characteristic to the individual species, as well as the blocked derivatives of such compounds are prepared by the pentafluorophenol method, i.e., the carboxy group of the acylating component is activated by converting it into pentafluorophenyl ester in the coupling reaction carried out with blocked peptides containing the aspartyl group or an aspartylglycine moiety. The acylation is carried out preferably using equimolar quantities of the respective reactants. The free peptides obtained after removing the blocking groups can be converted into their acid addition salts or pharmaceutically acceptable complexes or condensates.

Human adrenocorticotropic hormone and its derivatives are valuable substances of therapeutical activity.

1 Claim, No Drawings

PROCESS FOR THE PREPARATION OF BIOLOGICALLY ACTIVE POLYPEPTIDES CONTAINING ASPARTYL GROUP

This invention relates to a process for the preparation of biologically active polypeptides containing an aspartyl group, or an aspartyl-glycine moiety:

As it is known from the literature, when synthesizing aspartic peptides, the β-carboxamide group in Asparagine is converted by dehydration easily into a β-cyano-alanine derivative (M. Bodánszky, V. du Vigneaud: J. Am. Chem. Soc. 81, 5688 (1959); E. Schröder, K. Lübke: Peptides I. p. 110), and peptides containing an aspartyl moiety esterified on the β-carboxy group are converted easily into cyclic succinimide derivatives (E. Schröder, K. Lübke: Peptides I. p. 203; M. A. Ondetti et al.: Biochemistry 7, 4069 (1968)). This latter reaction proceeds particularly readily when the asparagine moiety is attached to a glycine moiety in the peptide chain. Thus, for example, the synthetic tetrapeptide Pro-Asn-Gly-Pro suffers complete desamination even in a 0.1 molar ammonia solution (L. Gráf et al.: Polypeptide Hormones, p. 225, Akadémia Kiadó, Budapest (1971)). In order to avoid these difficulties, carboxamide protecting groups are now more frequently utilized in the synthesis of peptides containing an aspartyl group (see e.g. W. König, R. Geiger: Ber. 103, 2041 (1970)), and no example can be found in the literature for acylation with an aspartylglycine sequence.

The fact that according to more recent studies the structure originally attributed to the adrenocorticotropic hormones should slightly be modified, can also be explained by the easy desamination of the carboxamide group of the aspartyl-glycine moiety. Namely, the systematic comparison of the natural and synthetic preparations led to the conclusion that the carboxamide group originally supposed to be in the 30 position is in fact in the 25 position, and a Gly-Ala sequence can be found in the 26 to 27 positions both in swine and in human adrenocorticotropic hormones. Accordingly, the correct structure of the human adrenocorticotropic hormone is apparently the following:

H-Ser-Tyr-Ser-Met-Glu-His-Phe-Arg-Trp-Gly-Lys-Pro-Val-
 1   2   3   4   5   6   7   8   9  10  11  12  13
-Gly-Lys-Lys-Arg-Arg-Pro-Val-Lys-Val-Tyr-Pro-Asn-Gly-
 14  15  16  17  18  19  20  21  22  23  24  25  26
-Ala-Glu-Asp-Glu-Ser-Ala-Glu-Ala-Phe-Pro-Leu-Glu-Phe-OH
 27  28  29  30  31  32  33  34  35  36  37  38  39

The synthesis of human adrenocorticotropic hormone having a structure as described by T. H. Lee et al. (J. Biol. Chem. 236, 2970 (1961)), as well as of the fragments of this hormone was first disclosed in Hung. Pat. No. 155 254, and in the corresponding foreign patent specifications, e.g. Brit. Pat. No. 1 201 053.

This invention relates to the synthesis of human adrenocorticotropic hormone of the above modified structure, as well as to the synthesis of its fragments characteristic to the individual species.

This invention is based on the discovery that the pentafluorophenol-method (L. Kisfaludy et al.: Proc. 8th Europ. Peptide Symp. 1966, p. 25 (1967), L. Kisfaludy et al.: J. Org. Chem. 35, 3563 (1970), J. Kovacs et al.: J. Am. Chem. Soc. 89, 183 (1967)), which has not been utilized so far in the synthesis of biologically active polypeptides, is, under certain conditions, particularly suitable for the synthesis of polypeptides containing an aspartyl group and having a structure similar to that described above.

We have found, unexpectedly, that when the reaction is carried out at a temperature of about 0°C, Z-Asn-OH can be converted into its pentafluorophenyl ester with a yield of at least 90 %, without blocking the carboxamide group. Z is a blocking group located on the α-amine. Under these conditions cyclic succinimide derivatives and β-cyano-alanine compounds practically do not form. The thus-obtained Z-Asn-OPFP can be used for the acylation of amino acid or peptide derivatives without the hazard of side reactions. Thus, for example, the blocked dipeptide Z-Asn-Gly-OtBu can be prepared from the above compound with a yield exceeding 90 %, and this latter product can be converted into Z-Asn-Gly-OH, by contacting it with trifluoroacetic acid. This latter dipeptide can also be converted into its pentafluorophenyl ester with an excellent yield, and the obtained ester can be used for the acylation of the peptides mentioned in the examples ($ACTH_{27-31}$, $ACTH_{27-32}$, $ACTH_{27-39}$). The acylation proceeds with an excellent yield, and side reactions do not occur.

The further advantage of the pentafluorophenyl method can be pointed out very clearly when synthesizing higher peptides containing an aspartyl group. According to our observations, pentafluorophenol evolving in the course of the acylation does not cause difficulties which can arise in many cases e.g. when the pentachlorophenol method is applied (British Patent Specification No. 1 201 053). A disadvantage of the pentachlorophenol method is that the coupling reaction leads to equilibrium, and an excessive amount of the amine compound or a tertiary base is required in order to prepare the desired product with an acceptable yield. Utilizing, however, the pentafluorophenol method, an excessive amount of a base is not necessary. This observation seemed to be in contradistinction with the fact that according to the literature, pentafluorophenol and pentachlorophenol have identical $p_k$ values ($p_k = 5.3$). We have found, however, that the $p_k$ values of these phenol derivatives markedly differ from each other in dimethylformamide medium; where pentachlorophenol shows a $p_k$ value of 5.05, while the respective value of pentafluorophenol is 6.35. In other words, pentafluorophenol dissociates in dimethylformamide to a lower extent than pentachlorophenol, consequently the stable protonation of the base component and the retardation of the coupling reaction do not occur.

A further advantage of the pentafluorophenol method resides in the fact that pentafluorophenol can easily be removed from the reaction product. The removal of pentachlorophenol or of its salts formed with organic bases is far more difficult, and the traces of these compounds remaining in the reaction mixture lead to the formation of hydrochloric acid in the subsequent catalytic hydrogenation step. The thus formed hydrochloric acid, however, damages the blocking groups sensitive to acids. On the other hand, pentafluorophenol can easily and quantitatively be removed by pouring the reaction mixture into ether so that the above disadvantages can be avoided.

From practical points of view it is an important advantage that pentafluorophenyl esters are far more soluble in organic solvents than the respective pentachlorophenyl compounds. Thus, for example, the amount of dimethylformamide solvent required in the preparation of Z-Asn-Gly-OPFP is only 10 % of that which would be necessary when preparing the respective pentachlorophenyl ester.

We have found further that the pentafluorophenol method is particularly suitable in the synthesis of higher peptides. According to recent publications (see e.g. R. Schwyzer, P. W. Schiller: Helv. Chim. Acta 54, 897 (1971), E. Wunsch: Ber. 104, 2445 (1971)), the reaction should be carried out at elevated temperatures and/or the acylating agent should be added in excess in order to obtain the desired products with better yields and with a higher degree of purity. Utilizing the pentafluorophenyl method, however, there is no need to use elevated temperatures or excessive amounts of the acylating agent in order to arrive at the same result. Thus, for example, when reacting the blocked decapeptide Z-Lys(BOC)-Lys(BOC)-Arg(NO₂)-Pro-Val-Lys(-BOC)-Val-Tyr(tBu)-Pro-OH with the heptapeptide H-Asn-Gly-Ala-Glu(OtBu)-Asp(OtBu)-Glu(OtBu)-Ser-(tBu)-(OtBu) or with the octapeptide H-Asn-Gly-Ala-Glu(OtBu)-Asp(OtBu)-Glu(OtBu)-Ser-Ala-OtBu at room temperature and in dimethylformamide solution in the presence of a complex of pentafluorophenol and dicyclohexyl carbodiimide, the reaction terminates practically within 5 to 6 hours (as determined by thin layer chromatography), and the blocked heptadecapeptide (15–31) or octadecapeptide (15–32) can be isolated simply and with a yield of at least 80 %. Similar excellent results can be reached when reacting the blocked ACTH 1–14 tetradecapeptide disclosed in Hung. Pat. No. 155 880 with the 15–31 heptadecapeptide, 15–32 octadecapeptide or 15–39 pentacosapeptide, respectively, under the same conditions as described above.

According to an alternative method, the aimed intermediates can also be prepared by acylating the pentapeptide H-Val-Lys(BOC)-Val-Tyr(tBu)-Pro-OH with the pentafluorophenyl ester of Z-Arg(NO₂)-Arg(NO₂)-Pro-OH, subjecting the obtained octapeptide to catalytic hydrogenation thus removing the nitro blocking groups of the guanidino radical of the arginine moiety, and synthesizing stepwise the blocked 15–24 decapeptide. The obtained compound differs from the blocked 15–24 decapeptide described above in that respect that the guanidino groups of the arginine moiety are present in protonated form. The advantage of this latter synthesis resides in the fact that the C-terminal peptides containing acid-sensitive blocking groups are not to be subjected to the catalytic hydrogenation used for the simultaneous removal of the nitro groups. As it is already known, this latter type of catalytic hydrogenation can only be carried out in an acetic acid medium, and requires a long reaction time (in some instances even several days).

Accordingly, this invention relates to a new method for the preparation of peptides representing the human adrenocorticotropic hormone and of its fragments having the general formula (I)

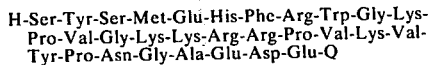

and of the blocked derivatives of such compounds, where Q may be one of the groups
a. Ser-OH,
b. Ser-Ala-OH,
c. Ser-Ala-Glu-OH,
d. Ser-Ala-Glu-Ala-OH,
e. Ser-Ala-Glu-Ala-Phe-OH,
f. Ser-Ala-Glu-Ala-Phe-Pro-OH,
g. Ser-Ala-Glu-Ala-Phe-Pro-Leu-OH,
h. Ser-Ala-Glu-Ala-Phe-Pro-Leu-Glu-OH,
i. Ser-Ala-Glu-Ala-Phe-Pro-Leu-Glu-Phe-OH.

According to the method of the invention, in the course of the coupling of the blocked intermediates, the carboxy group of the acylating component is activated by converting it into the pentafluorophenyl ester. The free peptides obtained after removing the blocking groups are converted into their acid addition salts or pharmaceutically acceptable complexes or condensates, respectively.

The starting compounds and the intermediates are prepared according to methods conventionally used in peptide chemistry. As amino blocking groups, benzyloxycarbonyl, tert-butoxycarbonyl or p-chlorobenzyloxycarbonyl groups may be used,, while the carboxy group is preferably blocked by ester formation, especially using methanol, ethanol or tert-butanol as the esterifying agent. If necessary, the hydroxy groups attached to the side chains can be blocked by ether formation, whereby tert-butanol or benzylalcohol can be used as etherifying agents. The guanidino group of the arginine moiety is preferably blocked by a nitro group; the protonation of the guanidino group, however, exerts also a proper blocking effect. By the proper selection of the individual blocking group it is possible to ensure that the group or groups could selectively or simultaneously be removed by acidolysis or hydrogenolysis.

The lower peptides can be synthetized stepwise or by fragment-condensation. The reaction can be carried out by the mixed anhydride, azide, activated ester or dicyclohexyl carbodiimide method.

The main feature of the invention is that when coupling peptides containing aspartyl group, the carboxy group of the acylating component is activated by converting it into its pentafluorophenyl ester. The pentafluorophenyl ester may be prepared in a separate step, or this acylating agent can be formed directly in the reaction mixture where the acylation takes place. The activated ester can be prepared by adding pentafluorophenol and dicyclohexyl carbodiimide into the reaction mixture. According to a particularly preferred method, the pentafluorophenol - dicyclohexyl carbodiimide complex is prepared in a separate step, and this complex is introduced into the reaction mixture in an amount of 1.2 to 1.5 moles. The advantage of this latter method is that the complex can be handled more easily, furthermore the possible sulfur-containing contaminations of dicyclohexyl carbodiimide, which may adversely affect the next hydrogenation step, can also be removed during the preparation of the complex.

The coupling reaction according to the invention proceeds with high yields and without the occurrence of side reactions. Consequently, it is not necessary to purify the blocked intermediates separately (e.g. by column chromatography), since a sufficiently pure compound can be obtained by the only purification of the deblocked end-product. The deblocked end-product can be purified e.g. by countercurrent distribution or by column chromatography, using e.g. several types of carboxymethyl cellulose as adsorbent.

The peptides prepared according to the invention can be converted into their acid addition salts and pharmaceutically acceptable complexes. The salts may be those formed with pharmaceutically acceptable acids, e.g. with acetic, hydrochloric, sulfuric or phosphoric acids or higher fatty acids. The term "pharmaceutically acceptable complexes" used in the specification and claims relates to compounds of the peptides formed with certain organic or mineral substances, said compounds possessing prolonged activity. The organic substances usable for the preparation of the complexes are e.g. the following: gelatines, carboxymethyl cellulose type compounds, alginic esters, amino acid polymers and other homo- and copolymers. Among the mineral substances, the slightly soluble salts of certain metals, especially of zinc, such as zinc phosphates or pyrophosphates, are to be mentioned. Compounds of prolonged activity can also be prepared by contacting the peptides with certain silicates, which form insoluble complexes or condensates with the peptide in question. The structure of these complexes or condensates has not yet been determined.

The peptides prepared according to the invention can be used in therapy in the form of conventional pharmaceutical products. Among the pharmaceutical products the following ones are to be mentioned: solid lyophilizates, containing inert carriers, e.g. mannitol, lactose, starch, etc. besides the active agent; suspensions and emulsions containing optionally inert preservatives, stabilizers and auxiliary substances. The active agent can also be used in the form of the above-mentioned complexes and condensates; due to their prolonged effect, such pharmaceutical products are particularly preferred.

The usual dose of the adrenocorticotropic hormones is 0.1 to 3.0 mg. The hormones can be administered subcutaneously, parenterally or intramuscularly, 1 to 7 times a week.

The process of the invention is elucidated in detail in the following non-limiting Examples. The intermediates described in the Examples are new substances.

The abbreviations used in the Examples are those accepted by IUPAC-IUB (J. Biol. Chem. 247, 977 (1972). The symbols indicated in brackets after the headlines contain the N-terminal and C-terminal groups and the numbering of the sequency. The protecting groups attached to the side chains are indicated in the headlines in brackets. The following other abbreviations were also used: DCC = dicyclohexyl carbodiimide, DCU = dicyclohexyl urea, PFPOH = pentafluorophenol, PCPOH = pentachlorophenol, DCHA = dicyclohexylamine, DMF = dimethyl formamide; Z = benzyloxycarbonyl group; ONSu = N-succinimide group.

The melting points were determined in a Dr. Tottoli type apparatus (Buchi, Schweiz). The thin layer chromatographical examinations were carried out on "Silicagel nach Stahl" adsorbent, in the following solvent mixtures:

1. Ethyl acetate-(pyridine-acetic acid-water=20:6:11)=95:5
2. Ethyl acetate-(pyridine-acetic acid-water=20:6:11)=9:1
3. Ethyl acetate-(pyridine-acetic acid-water=20:6:11)=4:1
4. Ethyl acetate-(pyridine-acetic acid-water=20:6:11)=3:2
5. Ethyl acetate-pyridine-acetic acid-water = 240:20:6:11
6. Ethyl acetate-pyridine-acetic acid-water = 120:20:6:11
7. Ethyl acetate-pyridine-acetic acid-water = 60:20:6:11
8. Ethyl acetate-pyridine-acetic acid-water = 30:20:6:11
9. Ethyl acetate-pyridine-acetic acid-water = 480:20:6:11
10. Chloroform - hexane - acetic acid = 8:1:1
11. Chloroform - methanol = 98:2
12. Chloroform - methanol = 95:5
13. Chloroform - methanol = 9:1
14. Chloroform - methanol = 85:5
15. n-Butanol - pyridine - acetic acid - water = 30:20:6:24
16. Chloroform - methanol - acetic acid = 8:1:1

The spots were developed with ninhydrine and/or with chlorine + tolidine.

EXAMPLE 1

Synthesis of human $ACTH_{1-31}$

Step 1: Z-Glu(OtBu)-Ser(tBu)-OtBu (Z-30-31-OtBu)

10.85 g. (25 mmoles) of Z-Glu(OtBu)-ONSu are dissolved in 100 ml. of ethyl acetate, and 7.0 g. (27.5 mmoles) of H-Ser(tBu)-OtBu.HCl are spread into the solution. The obtained suspension is cooled to 0°C, and 3.85 ml. (27.5 mmoles) of triethylamine are added to it with stirring. The reaction mixture is stirred for 0.5 hours at 0°C, thereafter stirring is continued at room temperature overnight. The mixture is washed successively with 2×20 ml. of n hydrochloric acid, 3×20 ml. of n $NaHCO_3$ and water. The ethylacetate solution is dried, evaporated to dryness, and the oily residue is triturated with petroleum ether. 10.45 g. (77.8 %) of Z-30-31-OtBu are obtained. M.p.: 92°–95°C, $R_f^{11} = 0.8$

| Analysis for $C_{28}H_{44}O_8N_2$ (536.68): | | |
|---|---|---|
| Calculated %: | C 62.7 | H 8.3 |
| Found %: | C 62.4 | H 8.2 |

Step 2: H-Glu(OtBu)-Ser(tBu)-OtBu (H-30-31-OtBu)

2.5 g. of palladium-on-carbon are added to the solution of 17.2 g. (32 mmoles) of Z-30-31-OtBu in 350 ml. of methanol, and gaseous hydrogen is bubbled into the mixture for 1 hour. The catalyst is removed by filtration, the filtrate is evaporated to dryness under reduced pressure, the solid residue is mixed with petroleum ether, and the mixture is filtered. 10.97 g. (83.4 %) of H-Glu(OtBu)-Ser(tBu)-OtBu are obtained. M.p.: 78°–82°C, $R_f^{11} = 0.4$.

| Analysis for $C_{20}H_{38}O_6N_2$ (402.54): | | |
|---|---|---|
| Calculated %: | C 59.7 | H 9.5 | N 6.9 |
| Found %: | C 59.8 | H 9.4 | N 6.6 |

Step 3: Z-Asp(OtBu)-Glu(OtBu)-Ser(tBu)-OtBu (Z-29-31-OtBu)

A solution of 9.45 g. (22.5 mmoles) of Z-Asp(OtBu)-ONSu and 10.1 g. (25 mmoles) of H-30-31-OtBu in 200 ml. of ethyl acetate is left to stand overnight, thereafter the solution is washed successively with 2×50 ml. of n hydrochloric acid, 3×50 ml. of n $NaHCO_3$ solution and water. The ethyl acetate is distilled off, and the oily residue is triturated with water. The solid is filtered off. 15.2 g. (95.0 %) of Z-29-31-OtBu are obtained. M.p.: 84°–87°C, $R_f^{11} = 0.70$.

| Analysis for $C_{36}H_{57}O_{11}N_3$ (707.88): | | |
|---|---|---|
| Calculated %: | C 61.1 % | H 8.1 |
| Found %: | C 61.3 | H 8.3 |

Step 4:
Z-Glu(OtBu)-Asp(OtBu)-Glu(OtBu)-Ser(tBu)-OtBu (Z-28-31-OtBu)

A mixture of 14.18 g. (20 mmoles) of Z-29-31-OtBu, 280 ml. of methanol and 2.1 g. of palladium-on-carbon is hydrogenated for 0.5 hours. The catalyst is filtered off, and the filtrate is evaporated to dryness under reduced pressure. The 11.65 g. of oily residue ($R_f^{11} = 0.2$) is reacted with 8.25 g. (19 mmoles) of Z-Glu(OtBu)-ONSu in 200 ml. of ethyl acetate. The solution is left to stand overnight, thereafter it is washed successively with 2×50 ml. of n hydrochloric acid, 3×50 ml. of n NaHCO₃ solution and water. The ethyl acetate solution is dried, the solvent is distilled off, the solid residue is triturated with n-hexane and filtered. The obtained crude product is dissolved in 43 ml. of hot ethyl acetate, and 7 ml. of n-hexane are added to the solution. The next day the separated crystals are filtered off and dried. 13.0 g. (76.5 %) of Z-28-31-OtBu are obtained. M.p.: 184°–185°C, $R_f^1 = 0.80$.

| Analysis for $C_{45}H_{72}O_{14}N_4$ (893.1): | | |
|---|---|---|
| Calculated %: | C 60.5 | H 8.1 |
| Found %: | C 60.8 | H 8.0 |

Step 5:
H-Glu(OtBu)-Asp(OtBu)-Glu(OtBu)-Ser(tBu)-OtBu (H-28-31-OtBu)

A solution of 12.5 g. (14 mmoles) of Z-28-31-OtBu in 250 ml. of methanol is hydrogenated for 0.5 hours in the presence of 1.8 g. of palladium-on-carbon. The catalyst is removed by filtration, and the filtrate is evaporated to dryness. The solid residue is triturated with n-hexane, and the mixture is filtered. 10.09 g. (95 %) of H-28-31-OtBu are obtained. M.p.: 130°–140°C, $R_f^{11} = 0.25$.

| Analysis for $C_{36}H_{66}O_{12}N_4$ (758.97): | |
|---|---|
| Calculated % | N 7.4 |
| Found | N 7.6 |

Step 6:
Z-Ala-Glu(OtBu)-Asp(OtBu)-Glu(OtBu)-Ser(tBu)-OtBu (Z-27-31-OtBu)

6.62 g. (8.7 mmoles) of H-28-31-OtBu are dissolved in 65 ml. of ethyl acetate, and 2.72 g. (8.5 mmoles) of Z-Ala-ONSu are added to the solution. After 5 minutes of stirring, a homogeneous solution is formed. The reaction mixture is stirred for one hour; at that time the product separates from the mixture. The mixture is left to stand overnight; thereafter the product is filtered off and washed with ethyl acetate. The crude product is recrystallized from 65 ml. of ethyl acetate. 6.61 g. (80.7 %) of Z-27-31-OtBu are obtained. M.p.: 193°–195°C, $R_f^{11} = 0.75$.

| Analysis for $C_{48}H_{77}O_{15}N_5$ (964.18): | | |
|---|---|---|
| Calculated %: | C 59.8 | H 8.1 |
| Found %: | C 59.6 | H 8.1 |

Step 7:
H-Ala-Glu(OtBu)-Asp(OtBu)-Glu(OtBu)-Ser(tBu)-OtBu (H-27-31-OtBu)

6.61 g. (6.85 mmoles) of Z-27-31-OtBu are dissolved in 150 ml. of methanol with gentle heating. The solution is cooled to room temperature; 1 g. of palladium-on-carbon is added to it, and gaseous hydrogen is bubbled into the mixture for 0.5 hours. The catalyst is removed by filtration, the filtrate is evaporated to dryness, the solid residue is triturated with n-hexane; and the mixture is filtered. 5.55 g. (97.6 %) of H-27-31-OtBu are obtained. M.p.: 138°–142°C, $R_f^2 = 0.15$.

| Analysis for $C_{40}H_{71}O_{13}N_5$ (830.05) | | | |
|---|---|---|---|
| Calculated %: | C 57.9 | H 8.6 | N 8.4 |
| Found %: | C 57.7 | H 8.3 | N 8.1 |

Step 8: Z-Asn-OPFP 1.33 g. (5 mmoles) of Z-Asn-OH and 3.04 g. of pentafluorophenol are dissolved in 3.5 ml. of DMF, and 10.5 ml. of dioxane are added to the solution. The solution is cooled to 0°C, and 1.13 g. (5.5 mmoles) of DCC are added with stirring. The reaction mixture is stirred at 0°C for 2 hours; thereafter the DCU is removed by filtration, and the filtrate is evaporated to dryness under reduced pressure. The residue is triturated with 8 ml. of ether. The obtained white, crystalline substance is filtered off, and washed with a small amount of cold ether and dried. 2.02 g. (93.3 %) of Z-Asn-OPFP are obtained. M.p.: 149°–150 °C. $R_f^{10} = 0.35$.

| Analysis for $C_{18}H_{13}O_5N_2F_5$ (432.31): | | | |
|---|---|---|---|
| Calculated %: | C 50.0 | H 3.0 | N 6.5 |
| Found %: | C 50.2 | H 3.1 | N 6.4 |

Step 9: Z-Asn-Gly-OtBu (Z-25-26-OtBu)

0.43 g. (1 mmole) of Z-Asn-OPFP are dissolved in 10 ml. of dioxane with gentle heating. The solution is cooled to 10°°C, and 0.185 g. (1.1 mmoles) of H-Gly-OtBu.HCl are added to it. 0.154 ml. (1.1 mmoles) of triethylamine are added to the obtained suspension with stirring, and the reaction mixture is stirred at room temperature for 0.5 hours. The solids are removed by filtration, and the filtrate is evaporated to dryness. The gelatinous residue is triturated with ether, and the solid is filtered off. 0.34 g. (89.8 %) of Z-Asn-Gly-OtBu are obtained. M.p.: 150°–151°C, $R_f^2 = 0.6$.

| Analysis for $C_{18}H_{25}O_6N_3$ (379.42): | |
|---|---|
| Calculated %: | N 11.1 |
| Found % : | N 11.2 |

Step 10: Z-Asn-Gly-OH (Z-25-26-OH)

9.13 g. (26 mmoles) of Z-Asn-Gly-OtBu are dissolved in 90 ml. of trifluoroacetic acid, and after 0.5 hours of standing 450 ml. of dry ether are added to the solution. The separated white precipitate is filtered off, washed with ether and crystallized from 35 ml. of water. 6.56 g. (78 %) of Z-Asn-Gly-OH are obtained. M.p.: 170°–172°C, $R_f^4 = 0.45$.

Step 11:
Z-Asn-Gly-Ala-Glu(OtBu)-Asp(OtBu)-Glu(OtBu)-Ser(tBu)-OtBu (Z-25-31-OtBu)

2.59 g. (8 mmoles) of Z-Asn-Gly-OH, 6.65 g. (8 mmoles) of H-Ala-Glu(OtBu)-Asp(OtBu)-Glu(OtBu)-Ser(tBu)-OtBu and 4.86 g. of pentafluorophenol are dissolved in 28 ml. of DMF. The solution is cooled to 0°C, and 1.81 g. (8.8 mmoles) of DCC are added to it. The reaction mixture is stirred at 0°C for 0.5 hours, and stirring is continued at room temperature for 2.5 hours. The separated DCU is removed by filtration; the filtrate is evaporated to dryness, and the residue is triturated with ethyl acetate. 7.3 g. (80.5 %) of Z-25-31-OtBu are obtained. M.p.: 194°C (under decomposition), $R_f^3 = 0.6$.

Step 12:
H-Asn-Gly-Ala-Glu(OtBu)-Asp(OtBu)-Glu(OtBu)-Ser(tBu)-OtBu (H-25-31-OtBu)

6.47 g. (5.7 mmoles) of Z-25-31-OtBu are dissolved in a mixture of 220 ml. of ethanol and 20 ml. of DMF, and gaseous hydrogen is bubbled into the mixture for 1 hour in the presence of 1 g. of palladium-on-carbon. The catalyst is removed by filtration, the filtrate is evaporated to dryness, and the gelly residue is triturated with ether. The solid is filtered off and washed. 4.9 g. (86.2 %) of H-25-31-OtBu are obtained. M.p.: 174°–176°C (under decomposition, $R_f^3 = 0.2$.

Step 13:
Z-Lys(BOC)-Arg(NO$_2$)-Arg(NO$_2$)-Pro-Val-Lys(BOC)-Val-Tyr(tBu)-Pro-Asn-Gly-Ala-Glu(OtBu)-Asp(OtBu)-Glu(OtBu)-Ser(tBu)-OtBu (Z-15-31-OtBu)

7.4 g. (4 mmoles) of Z-Lys(BOC)-Lys(BOC)-Arg(NO$_2$)-Arg(NO$_2$)-Pro-Val-Lys(BOC)-Val-Tyr(tBu)-Pro-OH (see Brit. Pat. No. 1 201 053) and 4.2 g. (4.2 mmoles) of H-25-31-OtBu are dissolved in 25 ml. of DMF. The solution is cooled to 0.°C, and 3.64 g. (4.8 mmoles) of DCC-PFPOH complex, containing the reactants in a ratio of 1:3, are added to it. The reaction mixture is stirred at 0°C for 20 minutes, and stirring is continued at room temperature for 5 hours. The mixture is filtered into 300 ml. of dry ether, and the separated precipitate is filtered off. 11.0 g. (97 %) of crude product are obtained, m.p.: 180°C. The crude product is dissolved in 33 ml. of methanol, and precipitated by adding 430 ml. of ethyl acetate. 8.75 g. (77 %) of Z-15-31-OtBu are obtained. M.p.: 185°C (under decomposition), $R_f^3 = 0.5$. Step 14: H-Lys(BOC)-Lys(BOC)-Arg-Arg-Pro-Val-Lys(BOC)-Val-Tyr(tBu)-Pro-Asn-Gly-Ala-Glu(OtBu)-Asp(OtBu)-Glu(OtBu)-Ser(tBu)-OtBu.3HCl (H-15-31 -OtBu.3HCl)

6.5 g. (2.3 mmoles) of Z-15-31-OtBu are dissolved in 85 ml. of acetic acid, and gaseous hydrogen is bubbled into the mixture in the presence of 2 g. of palladium-on-carbon. The progress of the reaction is monitored by thin layer chromatography. When the reaction terminates the catalyst is filtered off, and the filtrate is evaporated to dryness. The obtained 6.27 g. of product are dissolved in 70 ml. of water, and the solution is acidified to pH 4 with dilute hydrochloric acid under cooling. Thereafter 20 ml. of 30 % aqueous NaCl solution are added to the acidic mixture, and the separated precipitate is filtered off and dried. In order to remove the inorganic salt, the precipitate is suspended in a mixture of ethanol and chloroform, the insolubles are removed by filtration, and the filtrate is evaporated to dryness. The residue is triturated with ether and filtered. 5.35 g. (85.6 %) of H-15-31-OtBu.3HCl are obtained. $R_f^4 = 0.45$.

Step 15:
BOC-Ser-Tyr-Ser-Met-Glu-(OtBu)-His-Phe-Arg-Trp-Gly-Lys(BOC)-Pro-Val-Gly-Lys(BOC)-Lys(BOC)-Arg-Arg-Pro-Val-Lys(BOC)-Val-Tyr(tBu)-Pro-Asn-Gly-Ala-Glu(OtBu)-Asp(OtBu)-Glu(OtBu)-Ser(tBu)-OtBu-3HCl (BOC-1-31-OtBu. .3HCl)

2.96 g. (1.5 mmoles) of BOC-Ser-Tyr-Ser-Met-Glu(OtBu)-His-Phe-Arg-Trp-Gly-Lys(BOC)-Pro-Val-Gly-OH (Brit. Pat. No. 1 201 053) and 4.08 g. (1.5 mmoles) of H-15-31-OtBu. 3HCl are dissolved in 20 ml. of DMF. The solution is cooled to 0°C, and 0.21 ml. of triethylamine are added to it followed by 1.36 g. (1.8 mmoles) of DCC-PFPOH complex. The reaction mixture is kept at 0°C for 10 minutes, thereafter it is left to stand at room temperature overnight. The mixture is filtered into 250 ml. of dry ether, the separated precipitate is filtered off, washed with ether and dried. 6.84 g. (98.4 %) of BOC-1-31-OtBu-3HCl are obtained; $R_f^4 = 0.45$.

Step 16:
H-Ser-Tyr-Ser-Met-Glu-His-Phe-Arg-Trp-Gly-Lys-Pro-Val-Gly-Lys-Lys-Arg-Arg-Pro-Val-Lys-Val-Tyr-Pro-Asn-Gly-Ala-Glu-Asp-Glu-Ser-OH.3CH$_3$COOH (H-1-31-OH.3CH$_3$COOH)

3.0 g. (0.647 mmoles) of BOC-1-31-OtBu-3HCl are dissolved in 30 ml. of a 8:1:1 mixture of trifluoroacetic acid, water and anisole, and the solution is stirred at room temperature for one hour. Thereafter 300 ml. of ether are added to the solution, the separated precipitate is filtered and washed with ether. The obtained 2.89 g. of trifluoroacetate is dissolved in water, and the solution is passed through Dowex IX-8 anion exchanger (acetate). The effluent is poured onto a column containing 500 ml. of CM 23, and purification is carried out by gradient elution. The fractions containing the desired product are combined and freeze-dried. 1.64 g. (70 %) of H-1-31-OH are obtained. The product is chromatographically pure and possesses its complete biological activity.

Amino acid analysis: Lys 4.08 (4); His 1.0 (1); Arg 2.94 (3); Asp 2.01 (2); Met 0.78 (1); Ser 2.78 (3); Glu 3.07 (3); Pro 2.86 (3); Gly 2.97 (3); Ala 1.09 (1); Val 2.95 (3); Tyr 2.1 (2); Phe 1.09 (1).

EXAMPLE 2

Alternate method for the preparation of human ACTH$_{1-31}$

Step 1: Z-Arg(NO$_2$)-Arg(NO$_2$)-Pro-OPFP (Z-17-19-OPFP)

3.26 g. (5 mmoles) of Z-Arg(NO$_2$)-Arg(NO$_2$)-Pro-OH (Brit. Pat. No. 1 201 053) are dissolved in 30 ml. of DMF, and 5.31 g. (7 mmoles) of DCC-PFPOH complex are added to the solution. The reaction mixture is stirred at room temperature for 5 hours, the separated DCU is removed by filtration, and the filtrate is evaporated to dryness. The oily residue solidifies upon storage under ether. The precipitate is filtered off, and washed with ether. The obtained 3.8 g. (92.9 %) of crude product are dissolved in 11 ml. of tetrahydrofuran, and precipitated by adding 60 ml. of ether to the solution. 3.42 g. (83.6 %) of Z-17-19-OPFP are obtained, $R_f = 0.55$.

| Analysis for $C_{31}H_{36}O_{10}N_{11}F_5$ (817.9): | |
|---|---|
| Calculated %: | N 18.8 |
| Found %: | N 18.6 |

Step 2:
Z-Arg($NO_2$)-Arg($NO_2$)-Pro-Val-Lys(BOC)-Val-Tyr(tBu)-Pro-OH (Z-17-24-OH)

2.22 g. (2.92 mmoles) of H-Val-Lys(BOC)-Val-Tyr(tBu)-Pro-OH (Brit. Pat. No. 1 201 053) are suspended in 25 ml. of DMF, and 2.64 g. (3.22 mmoles) of Z-17-19-OPFP are added to the suspension with stirring. After 2.5 hours' stirring at room temperature, a clear solution is formed. The solution is stirred for an additional 2.5 hours, thereafter it is evaporated to dryness. The obtained 3.8 g. (93.3 %) of crude product are dissolved in 15 ml. of methanol, and 100 ml. of ethyl acetate are added to the solution. The separated precipitate is filtered off and dried. 3.53 g. (87.2 %) of Z-17-24-OH are obtained, $R_f^4 = 0.7$.

Step 3:
H-Arg-Arg-Pro-Val-Lys(BOC)-Val-Tyr(tBu)-Pro-OH.3HCl (H-17-24-OH.3HCl)

0.4 g. (0.29 mmoles) of Z-17-24-OH are dissolved in 8 ml. of acetic acid, and the mixture is hydrogenated in the presence of 0.1 g. of palladium-on-carbon. The process of the reaction is monitored by thin layer chromatography. When the reaction terminates, the catalyst is filtered off and the filtrate is evaporated to dryness. The oily residue is dissolved in 3 ml. of methanol, and the solution is acidified to pH 4 with dilute hydrochloric acid under cooling. The acidic solution is evaporated to dryness, and the residue is triturated with ethyl acetate. 0.26 g. (70.2 %) of H-17-24-OH.3HCl are obtained, $R_f^4 = 0.1$.

Step 4:
Z-Lys(BOC)-Arg-Arg-Pro-Val-Lys(BOC)-Val-Tyr(tBu)-Pro-OH.2HCl (Z-16-24-OH.2HCl)

0.65 g. (0.49 mmoles) of H-17-24-OH.3HCl are suspended in 7 ml. of DMF, and 0.07 ml. of triethylamine and 0.3 g. (0.6 mmoles) of Z-Lys(BOC)-ONP are added to the suspension. The reaction mixture is stirred at room temperature for 24 hours, thereafter it is evaporated to dryness. The residue is triturated with ethyl acetate, filtered and washed with a small amount of water. 0.6 g. (76.3 %) of Z-16-24-OH.2HCl are obtained; $R_f^4 = 0.45$.

Step 5:
Z-Lys(BOC)-Lys(BOC)-Arg-Arg-Pro-Val-Lys(BOC)-Val-Tyr(tBu)-Pro-OH.2HCl (Z-15-24-OH.2HCl)

A solution of 0.5 g. (0.3 mmoles) of Z-16-24-OH.2HCl in 20 ml. of methanol is hydrogenated in the presence of palladium-on-carbon. When the reaction is over the catalyst is filtered off, and the filtrate is evaporated to dryness. The residue is triturated with ethyl acetate and filtered. 0.42 g. (97.3 %) of H-16-24-OH.2HCl are obtained; $R_f^4 = 0.15$. 0.33 g. (0.23 mmoles) of the obtained product are suspended in 3 ml. of DMF, and 0.14 g. (0.25 mmoles) of Z-Lys(BOC)-OPFP are added to the suspension. After 10 minutes of stirring a clear solution is formed. The solution is stirred for additional 3 hours, thereafter it is evaporated to dryness. The residue is triturated with ethyl acetate. 0.36 g. (85.4 %) of Z-15-24-OH.2HCl are obtained; $R_f^4 = 0.45$.

Step 6:
Z-Lys(BOC)-Lys-(BOC)-Arg-Arg-Pro-Val-Lys(BOC)-Val-Tyr(tBu)-Pro-Asn-Gly-Ala-Glu(OtBu)-Asp(OtBu)-Glu(OtBu)-Ser(tBu)-OtBu.2HCl (Z-15-31-OtBu.2HCl)

0.18 g. (0.1 mmoles) of Z-15-24-OH.2HCl and 0.10 g. (0.1 mmoles) of H-25-31-OtBu are dissolved in 1 ml. of DMF, and 0.091 g. (0.12 mmoles) of DCC-PFPOH complex are added to the solution. After 5 hours of stirring, the reaction mixture is diluted with ethyl acetate, the separated DCU is removed by filtration, and the filtrate is evaporated to dryness. The residue is triturated with ether. 0.25 g. (88.8 %) Z-15-31-OtBu.2HCl are obtained ($R_f^4 = 0.5$), which is further processed as described in Example 1.

EXAMPLE 3

Synthesis of human $ACTH_{1-32}$

Step 1: Z-Glu(OtBu)-Ser-Ala-OtBu (Z-30-32-OtBu)

23.9 g. (100 mmoles) of Z-Ser-OH and 14.5 g. (100 mmoles) of H-Ala-OtBu are dissolved in 150 ml. of methylene chloride. The solution is cooled to −10°C, and a solution of 20.6 g. (100 mmoles) of DCC in 100 ml. of methylene chloride is added dropwise to it. The reaction mixture is stirred at 0°C for 2 hours, thereafter it is left to stand overnight. The next day the separated DCU is filtered off, and the filtrate is washed successively with 3×70 ml. of n hydrochloric acid, 3×70 ml. of 5% $NaHCO_3$ solution and water. The organic phase is dried; methylene chloride is distilled off, and the oily residue is triturated with nhexane. The obtained 30.0 g. (82 %) of crude Z-Ser-Ala-OtBu are dissolved in 600 ml. of methanol, and the solution is hydrogenated in the presence of 2 g. of palladium-on-carbon. The progress of the reaction is monitored by thin layer chromatography. When the reaction terminates, the catalyst is filtered off, the filtrate is evaporated to dryness, and the oily residue is dissolved in 220 ml. of ethyl acetate. 33.0 g. (76 mmoles) of Z-Glu(OtBu)-ONSu are added to the ethyl acetate solution. The next day the solution is washed successively with 3×50 ml. of n hydrochloric acid, 3×50 ml. of 5% $NaHCO_3$ solution and water. The ethyl acetate solution is dried, the solvent is distilled off, and the oily residue is crystallized from a mixture of ethyl acetate and petroleum ether. 31.5 g. (75 %) of Z-30-32-OtBu are obtained. M.p.: 72°–74°C; $R_f^{11} = 0.6$; $[\alpha]_D = -28.9°$.

| Analysis for $C_{27}H_{41}N_3O_9$ (551.84): | | |
|---|---|---|
| Calculated %: | C 58.8 | H 7.5 | N 7.7 |

| Found %: | C 58.8 | H 7.7 | N 7.8 |

Step 2: H-Glu(OtBu)-Ser-Ala-OtBu (H-30-32-OtBu)

16.0 g. (29 mmoles) of Z-30-32-OtBu are dissolved in 350 ml. of methanol, and the solution is hydrogenated in the presence of 1.6 g. of palladium-on-carbon. When the reaction terminates, the catalyst is removed by filtration, and the filtrate is evaporated to dryness. The residue is crystallized from a mixture of methanol and ether. 9.06 g. (75 %) of H-30-32-OtBu are obtained. M.p.: 135°–136°C, $R_f^{11} = 0.15$, $[\alpha]_D = -25.9°$ (c = 1, in ethanol).

Analysis for $C_{19}H_{35}N_3O_7$ (417.80):
| Calculated %: | C 54.6 | H 8.5 | N 10.1 |
| Found %: | C 54.5 | H 8.4 | N 9.8 |

Step 3: Z-Asp(OtBu)-Glu(OtBu)-Ser-Ala-OtBu (Z-29-32-OtBu)

A solution of 8.2 g. (19.6 mmoles) of H-30-32-OtBu and 8.0 g. (19.0 mmoles) of Z-Asp(OtBu)-ONSu in 80 ml. of ethyl acetate is reacted overnight. The next day the solution is washed successively with 3×20 ml. of n hydrochloric acid, 3×20 ml. of 5% NaHCO$_3$ solution and water. The ethyl acetate solution is dried, the solvent is distilled off, the residue is triturated with petroleum ether and filtered. 12.08 g. (85.5 %) of Z-29-32-OtBu are obtained. M.p.: 85°–87°C; $R_f^{11} = 0.55$; $[\alpha]_D = -32.8°$ (c = 1, in ethanol).

Analysis for $C_{35}H_{54}O_{12}N_4$ (722.81):
| Calculated %: | C 58.2 | H 7.5 | N 7.8 |
| Found %: | C 58.3 | H 7.6 | N 7.3 |

Step 4: H-Asp(OtBu)-Glu(OtBu)-Ser-Ala-OtBu (H-29-32-OtBu)

A solution of 10.5 g. (14.5 mmoles) of Z-29-32-OtBu in 130 ml. of methanol is hydrogenated in the presence of 1 g. of palladium-on-carbon. When the reaction terminates, the catalyst is removed by filtration, and the filtrate is evaporated to dryness. The residue is triturated with petroleum ether. 8.35 g. (97.5 %) of H-29-32-OtBu are obtained. M.p.: 81-82°C; $R_f^{11} = 0.1$; $[\alpha]_D = -24.3°$ (c = 1, in ethanol).

Step 5: Z-Glu(OtBu)-Asp(OtBu)-Glu(OtBu)-Ser-Ala-OtBu (Z-28-32-OtBu)

A solution of 5.0 g. (11.5 mmoles) of Z-Glu(OtBu)-OnSu and 6.6 g. (11.2 mmoles) of H-29-32-OtBu in 100 ml. of chloroform is reacted overnight. The next day the reaction mixture is washed successively with 3×30 ml. of n hydrochloric acid, 3×30 ml. of NaHCO$_3$ solution and water. The chloroform solution is dried, the solvent is distilled off, and the residue is purified by precipitation from chloroform with petroleum ether. 8.45 g. (83 %) of Z-28-32-OtBu are obtained. M.p.: 168°–169°C; $R_f^{11} = 0.5$; $[\alpha]_D = -29°$ (c = 1, in ethanol).

Analysis for $C_{44}H_{69}N_5O_{15}$ (908.07)
| Calculated %: | C 58.2 | H 7.7 | N 7.7 |
| Found %: | C 58.4 | H 7.7 | N 7.5 |

Step 6: H-Glu(OtBu)-Asp(OtBu)-Glu(OtBu)-Ser-Ala-OtBu (H-28-32-OtBu)

A solution of 8.0 g. (8.8 mmoles) of Z-28-32-OtBu in 160 ml. of methanol is hydrogenated in the presence of 1 g. of palladium-on-carbon. When the reaction terminates, the catalyst is filtered off, the filtrate is evaporated to dryness, and the residue is triturated with ether and petroleum ether. 6.4 g. (94 %) of H-28-32-OtBu are obtained. M.p.: 138-139°C; $R_f^{12} = 0.1$; $[\alpha]_D = -9.7°$ (c = 1, in ethanol).

Step 7: Z-Ala-Glu(OtBu)-Asp(OtBu)-Glu(OtBu)-Ser-Ala-OtBu (Z-27-32-OtBu)

A solution of 5.2 g. (6.7 mmoles) of H-28-32-OtBu and 2.15 g. (6.7 mmoles) of Z-Ala-ONSu in 50 ml. of chloroform is reacted overnight. The next day the reaction mixture is washed succesively with 3×10 ml. of n hydrochloric acid, 3×10 ml. of 5% NaHCO$_3$ solution and water. The chloroform solution is dried, the solvent is distilled off, the residue is triturated with petroleum ether and filtered. 6.1 g. (93.1 %) of Z-27-32-OtBu are obtained. M.p.: 194°–195°C; $R_f^{12} = 0.5$; $[\alpha]_D = 30.9°$ (c = 1, in ethanol).

Analysis for $C_{47}H_{74}O_{16}N_6$ (979.14):
| Calculated %: | C 57.7 | H 7.6 | N 8.6 |
| Found %: | C 57.6 | H 7.7 | N 8.5 |

Step 8: H-Ala-Glu(OtBu)-Asp(OtBu)-Glu(OtBu)-Ser-Ala-OtBu (H-27-32-OtBu)

A solution of 6.1 g. (6.2 mmoles) of Z-27-32-OtBu in 120 ml. of methanol is hydrogenated in the presence of 1 g. of palladium-on-carbon. When the reaction terminates, the catalyst is filtered off, and the filtrate is evaporated to dryness. The residue is crystallized from a mixture of ethanol and ether. 4.35 g. (83 %) of H-27-32-OtBu are obtained. M.p.: 192°–194°C; $R_f^{12} = 0.25$; $R_f^3 = 0.1$.

Analysis for $C_{39}H_{68}N_6O_{14}$ (845.0):
| Calculated %: | C 55.4 | H 8.1 | N 9.9 |
| Found %: | C 55.2 | H 7.8 | N 9.6 |

Step 9: Z-Asn-Gly-Ala-Glu(OtBu)-Asp(OtBu)-Glu(OtBu)-Ser-Ala-OtBu (Z-25-32-OtBu)

2.45 g. (13.3 mmoles) of pentafluorophenol, 1.31 g. (4.02 mmoles) of Z-Asn-Gly-OH (see Example 1) and 5.4 g. (4.02 mmoles) of H-27-32-OtBu are dissolved in 24 ml. of dry DMF, thereafter the solution is cooled to 0°C, and 0.915 g. (4.43 mmoles) of DCC are added to it. The reaction mixture is stirred at 0°C for 0.5 hours and at room temperature for 2.5 hours. The separated DCU is filtered off, and the filtrate is evaporated to dryness. The solid residue is triturated with ethyl acetate, filtered, and washed with hot ethyl acetate. 4.12 g. (89 %) of Z-25-32-OtBu are obtained. M.p.: 200°–201°C; $R_f^3 = 0.6$; $[\alpha]_D = -13.9°$ (c = 1, in DMF).

Step 10:
H-Asn-Gly-Ala-Glu(OtBu)-Asp(OtBu)-Glu(OtBu)-Ser-Ala-OtBu (H-25-32-OtBu)

A solution of 4.0 g. (3.48 mmoles) of Z-25-32-OtBu in 140 ml. of methanol is hydrogenated in the presence of 0.5 g. of palladium-on-carbon. When the reaction terminates, the catalyst is filtered off; the filtrate is evaporated to dryness; the residue is triturated with ether and filtered off. 3.4 g. (96 %) of H-25-32-OtBu are obtained. M.p.: 188°–190°C; $R_f^4 = 0.5$; $[\alpha]_D = -6.6°$ (c = 0.89, in DMF).

Step 11:
Z-Lys(BOC)-Lys(BOC)-Arg(NO₂)-Arg(NO₂)-Pro-Val-Lys(BOC)-Val-Tyr(tBu)-Pro-Asn-Gly-Ala-Glu(OtBu)-Asp(OtBu)-Glu(OtBu)-Ser-Ala-OtBu (Z-15-32-OtBu)

3.0 g. (2.95 mmoles) of H-25-32-OtBu and 5.46 g. (2.95 mmoles) of Z-Lys(BOC)-Lys(BOC)-Arg(NO₂)-Arg(NO₂)-Pro-Val-Lys(BOC)-Val-Tyr(tBu)-Pro-OH (Brit. Pat. No. 1 201 053) are dissolved in 33 ml. of DMF. The solution is cooled to 0°C, and 3.35 g. (4.42 mmoles) of DCC-PFPOH complex are added to it. The reaction mixture is kept at 0°C for 15 minutes, thereafter at room temperature for 6 hours. The separated DCU is filtered off, and the filtrate is passed into 450 ml. of dry ether. The separated crude product is filtered off and purified by precipitation from methanol with ether. 7.18 g. (85.1 %) of Z-15-32-OtBu are obtained. $R_f^3 = 0.35$; $[\alpha]_D = -26.4°$ (c = 0.42, in DMF).

Step 12:
H-Lys(BOC)-Lys(BOC)-Arg(NO₂)-Arg(NO₂)-Pro-Val-Lys(BOC)-Val-Tyr(tBu)-Pro-Asn-Gly-Ala-Glu(OtBu)-Asp(OtBu)-Glu(OtBu)-Ser-Ala-OtBu.3HCl (H-15-32-OtBu.3HCl)

A solution of 6.5 g. (2.28 mmoles) of Z-15-32-OtBu in 85 ml. of acetic acid is hydrogenated in the presence of 2 g. of palladium-on-carbon. The progress of the reaction is monitored by thin layer chromatography. When the reaction terminates, the catalyst is filtered off, the filtrate is evaporated to dryness, the oily residue is triturated with dry ether, and the solid product is filtered off. This product is dissolved in 70 ml. of water, and the solution is acidified to pH 4 with dilute hydrochloric acid. The product is precipitated from the acidic solution by adding 30% NaCl solution. The precipitate is filtered off, and the inorganic salt is removed by precipitation from a mixture of methanol and chloroform. The solvent is distilled off, and the residue is triturated with ether. 5.6 g. (89.6 %) of H-15-32-OtBu-3HCl are obtained. $R_f^4 = 0.35$; $[\alpha]_D = -26.1°$ (c = 1, in DMF).

Amino acid analysis: Lys 3.0 (3); Arg 1.8 (2); Asp 1.98 (2); Ser 1.0 (1); Glu 2.2 (2); Pro 2.1 (2); Gly 1.05 (1); Ala 2.0 (2); Val 1.96 (2); Tyr 0.96 (1).

Step 13:
BOC-Ser-Tyr-Ser-Met-Glu(OtBu)-His-Phe-Arg-Trp-Gly-Lys(BOC)-Pro-Val-Gly-Lys(BOC)-Lys(BOC)-Arg-Arg-Pro-Val-Lys(BOC)-Val-Tyr(tBu)-Pro-Asn-Gly-Ala-Glu(OtBu)-Asp(OtBu)-Glu(OtBu)-Ser-Ala-OtBu.3HCl (BOC-1-32-OtBu-3HCl)

3.11 g. (1.57 mmoles) of BOC-Ser-Tyr-Ser-Met-Glu(OtBu)-His-Phe-Arg-Trp-Gly-Lys(BOC)-Pro-Val-Gly-OH.HCl (Brit. Pat. No. 1 201 053) and 4.30 g. (1.57 mmoles) of H-15-32-OtBu are dissolved in 25 ml. of DMF, and 0.22 ml. of triethylamine are added to the solution, followed by 1.79 g. (2.36 mmoles) of DCC-PFPOH complex. The reaction mixture is stirred for 24 hours at room temperature; thereafter it is filtered into 300 ml. of dry ether. The separated product is filtered off and washed. 7.2 g. (98.5 %) of BOC-1-32-OtBu-3HCl are obtained. $R_f^5 = 0.5$; $[\alpha]_D = -27.6°$ (c = 1, in DMF).

Step 14:
H-Ser-Tyr-Ser-Met-Glu-His-Phe-Arg-Trp-Gly-Lys-Pro-Val-Gly-Lys-Lys-Arg-Arg-Pro-Val-Lys-Val-Tyr-Pro-Asn-Gly-Ala-Glu-Asp-Glu-Ser-Ala.3CH₃COOH (H-1-32-OH.3CH₃COOH)

3.0 g. (0.64 mmoles) of BOC-1-32-OtBu-3HCl are dissolved with stirring in a mixture of 3.0 ml. of anisol, 3.0 ml. of water and 24 ml. of trifluoroacetic acid. After one hour of stirring, 300 ml. of ether are poured into the reaction mixture, the separated precipitate is filtered off and washed with ether. The obtained 2.86 g. of trifluoroacetate is dissolved in water, and passed through 100 ml. of a Dowex 1x-8 anion exchanger (acetate form). The effluent is poured onto a column of 500 ml. CM 23, and the column chromatographical purification is carried out by gradient elution. The fractions containing the main product are combined and freeze-dried. 1.7 g. (70 %) of H-1-32-OH are obtained. The product is chromatographically pure and possesses its complete biological activity.

Amino acid analysis: Lys 3.94 (4); His 1.0 (1); Arg 2.81 (3); Asp 2.07 (2); Met. 0.72 (1); Ser 2.72 (3); Glu 2.94 (3); Pro 2.96 (3); Gly 2.89 (3); Ala 2.2 (1); Val 2.97 (3); 2.89 1.98 (2); Phe 0.99 (1).

EXAMPLE 4

Synthesis of human ACTH

Step 1:
Z-Ser-Ala-Glu(OtBu)-Ala-Phe-Pro-Leu-Glu(OtBu)-Phe-OtBu (Z-31-39-OtBu)

A solution of 31.6 g. (48.3 mmoles) of Z-Leu-Glu(OtBu)-Phe-OtBu (S. Bajusz, T. Lazar: Acta Chim. Hung. 48, 111 (1966) in 310 ml. of DMF is hydrogenated in the presence of palladium-on-carbon catalyst. When the reaction terminates, the catalyst is filtered off, and the filtrate is evaporated to 100 ml. The concentrate is cooled to −20°C.

38.35 g. (74.4 mmoles) of Z-Ser-Ala-Glu(OtBu)-Ala-Phe-Pro-OH (see Brit. Pat. No. 1 201 053) are dissolved in 100 ml. of dry DMF, and 5.27 ml. (47.4 mmoles) of N-methyl-morpholine are added to the solution. Thereafter 6.26 ml. (47.7 mmoles) of isobutyl chloroformate are added to the stirred mixture at −10°C. The reaction mixture is stirred at −10°C for 8 minutes, then it is cooled to −20°C, and added with the pre-cooled concentrate prepared as described above. The reaction mixture is stirred at −10°C for 15 minutes then at 0°C for 1 hour, finally at room temperature for one hour. The mixture is poured into 2 liters of ice water containing 45 ml. of N-methyl-morpholine. The separated precipitate is filtered off, washed with dilute citric acid solution, water and finally with ether, and dried. 55.85 g. (89.9 %) of Z-31-39-OtBu are obtained. M.p.: 180°C (under decomposition), $R_f^5 = 0.7$.

Step 2:
H-Ser-Ala-Glu(OtBu)-Ala-Phe-Pro-Leu-Glu(OtBu)-Phe-OtBu (H-31-39-OtBu)

78.95 g. (60.15 mmoles) of Z-31-39-OtBu are dissolved in 1500 ml. of 80 % acetic acid, and the mixture is hydrogenated in the presence of palladium-on-carbon. When the reaction terminates, the catalyst is filtered off, and the filtrate is evaporated to dryness. The residue is triturated with ether and filtered. 74.35 g. (99 %) of H-31-39-OtBu are obtained. M.p.: 105°C (under decomposition), $R_f^7 = 0.5$.

Step 3:
Z-Glu(OtBu)-Ser-Ala-Glu(OtBu)-Ala-Phe-Pro-Leu-Glu(OtBu)-Phe-OtBu (Z-30-39-OtBu)

44.5 g. (85.8 mmoles) of Z-Glu(OtBu)-OH.DCHA salt are suspended in 450 ml. of dry DMF, and 9.6 ml. (85.5 mmoles) of N-methyl-morpholine are added to the suspension. The obtained solution is cooled to −10°C, and 11.3 ml. (85.8 mmoles) of isobutyl chloroformate are added dropwise to the stirred solution. The mixture is cooled to −20°C, and a −20°C solution of 88.5 g. (71.5 mmoles) of H-31-39OtBu in 300 ml. of dry DMF is poured into it. The reaction mixture is stirred at −10°C for 15 minutes, at 0°C for 1 hour and finally at room temperature for 1 hour, thereafter it is poured into 8 liters of n citric acid solution. The separated precipitate is filtered off, washed with water and ether, and dried. 104.1 g. (97.2 %) of Z-30-39-OtBu are obtained. M.p.: 136°–138°C (under decomposition), $R_f^5 = 0.8$.

Step 4:
H-Glu(OtBu)-Ser-Ala-Glu(OtBu)-Ala-Phe-Pro-Leu-Glu(OtBu)-Phe-OtBu (H-30-39-OtBu 103.1 g. (68.8 mmoles) of Z-30-39-OtBu are dissolved in 1500 ml. of 80 % acetic acid, and the mixture is hydrogenated in the presence of palladium-on-carbon. When the reaction terminates, the catalyst is filtered off, and the filtrate is evaporated to dryness. The obtained residue is triturated with ether, filtered, and washed with ether. 90.75 g. (92.7 %) of H-30-39-OtBu are obtained. M.p.: 118°C (under decomposition), $R_f^6 = 0.5$.

Step 5:
Z-Asp(OtBu)-Glu(OtBu)-Ser-Ala-Glu(OtBu)-Ala-Phe-Pro-Leu-Glu(OtBu)-Phe-OtBu (Z-29-39-OtBu)

38.3 g. (75.9 mmoles) of Z-Asp(OtBu)-OH.DCHA salt are suspended in 400 ml. of dry DMF. 8.5 ml. (76.6 mmoles) of N-methyl-morpholine are added to the suspension, then the obtained mixture is colled to −10 °10and 10 ml. (75.9 mmoles) of isobutyl chloroformate are added dropwise to the stirred mixture. The reaction mixture is cooled to −20°C, and a −20°C solution of 90 g. (63.25 mmoles) of H-30-39-OtBu in 250 ml. of DMF is added. The mixture is stirred at −10°C for 15 minutes, at 0°C for 1 hour, finally at room temperature for 1 hour. The separated salt is removed by filtration, and the filtrate is evaporated to dryness. The residue is triturated with n citric acid solution, the solid is filtered off, and washed until neutral. 98.5 g. (93 %) of Z-29-39-OtBu are obtained. M.p.: 185°C (under decomposition), $R_f^5 = 0.8$.

Step 6:
H-Asp(OtBu)-Glu(OtBu)-Ser-Ala-Glu(OtBu)-Ala-Phe-Pro-Leu-Glu(OtBu)-Phe-OtBu (H-29-39-OtBu)

67.25 g. (42.15 mmoles) of Z-29-39-OtBu are dissolved in 1300 ml. of 80 % acetic acid, and the mixture is hydrogenated in the presence of palladium-on-carbon. At the end of the reaction the catalyst is filtered off, and the filtrate is evaporated to dryness. The residue is triturated with ether, the solid is filtered off, and dried. 63.8 g. (95%) of H-29-39OtBu are obtained. M.p.: 128°–132°C (under decomposition), $R_f^5 = 0.3$.

Step 7:
Z-Glu(OtBu)-Asp(OtBu)-Glu(OtBu)-Ser-Ala-Glu(OtBu)-Ala-Phe-Pro-Leu-Glu(OtBu)-Phe-OtBu (Z-28-39-OtBu)

27.3 g. (52.55 mmoles) of Z-Glu(OtBu)-OH.DCHA salt are suspended in 270 ml. of dry DMF, and 5.9 ml. (53.2 mmoles) of N-methyl-morpholine are added to the suspension. The mixture is cooled to −10°C, and 6.95 ml. (52.55 mmoles) of isobutyl chloroformate are added dropwise into the stirred mixture. After 8 minutes of stirring, the mixture is cooled to −20°C, and added with a −20°C solution of 69.9 g. (43.8 mmoles) of H-29-39-OtBu in 270 ml. of DMF. The mixture is kept at −10°C for 15 minutes, at 0°C for 1 hour, finally at room temperature for 1 hour. The separated salt is removed by filtration, and the filtrate is evaporated to dryness. The residue is triturated with n citric acid solution, filtered, and washed until neutral. 70.15 g. (86.2 %) of Z-29-39-OtBu are obtained. M.p.: 205°C (under decomposition), $R_f^{13} = 0.9$.

Step 8:
Z-Ala-Glu(OtBu)-Asp(OtBu)-Glu(OtBu)-Ser-Ala-Glu(OtBu)-Ala-Phe-Pro-Leu-Glu(OtBu)-Phe-OtBu (Z-27-39-OtBu)

69.0 g. (37.2 mmoles) of Z-28-39-OtBu are dissolved in 1800 ml. of dry DMF, and the mixture is hydrogenated in the presence of palladium-on-carbon. At the end of the reaction the catalyst is removed by filtration, and the filtrate is concentrated to a final volume of 300 ml. The concentrate is stirred, and 20.2 g. (42.85 mmoles) of Z-Ala-OPCP are added to it, followed by the portionwise addition of 4.76 ml. (42.85 mmoles) of N-methyl-morpholine. The next day the thick, gelly mixture is poured into 4 liters of 5% $NaHCO_3$ solution with stirring and cooling. The separated solid is filtered off, and washed until neutral. The crude product is dissolved in 1900 ml. of hot methanol, and the product is precipitated from the solution by adding 1100 ml. of water. The mixture is left to stand overnight, thereafter the separated solid is filtered off, washed and dried. 59.2 g. (82.6 %) of Z-27-39-OtBu are obtained. M.p.: 210°C; $R_f^{12} = 0.7$.

Step 9:
H-Ala-Glu(OtBu)-Asp(OtBu)-Glu(OtBu)-Ser-Ala-Glu(OtBu)-Ala-Phe-Pro-Leu-Glu(OtBu)-Phe-OtBu (H-27-39-OtBu)

8.5 g. 4.41 mmoles) of Z-27-39-OtBu are dissolved in 850 ml. of dry DMF, and the mixture is hydrogenated in the presence of palladium-on-carbon. At the end of the reaction, the catalyst is removed by filtration; the filtrate is evaporated to dryness, and the residue is triturated with ether. 7.65 g. (96.9 %) of H-27-39-OtBu are obtained. M.p.: 197°C (under decomposition), $R_f^{12}$ = 0.3.

Step 10:
Z-Asn-Gly-Ala-Glu(OtBu)-Asp(OtBu)-Glu(OtBu)-Ser-Ala-Glu(OtBu)-Ala-Phe-Pro-Leu-Glu(OtBu)-Phe-OtBu (Z-25-39-OtBu 3.58 g. (2.0 mmoles) of H-27-39-OtBu and 0.65 g. (2.0 mmoles) of Z-Asn-Gly-OH (see Example 1) are dissolved in 30 ml. of dry DMF. The solution is cooled to 0°C, and 1.8 g. (2.4 mmoles) of DCC-PFPOH complex are added to it. After 4 hours of stirring, the mixture is filtered into 300 ml. of ether, the separated precipitate is collected by filtration, and washed with ether. 3.7 g. (88 )%) of Z-25-39-OtBu are obtained. M.p.: 194°C (under decomposition); $R_f^{12}$ = 0.3.

Step 11:
H-Asn-Gly-Ala-Glu(OtBu)-Asp(OtBu)-Glu(OtBu)-Ser-Ala-Glu(OtBu)-Ala-Phe-Pro-Leu-Glu(OtBu)-Phe-OtBu.HCl H-25-39-OtBu.HCl 3.92 g. (1.87 mmoles) of Z-25-39-OtBu are dissolved in 400 ml. of 80 % acetic acid, and the mixture is hydrogenated in the presence of palladium-on-carbon. At the end of the reaction the catalyst is filtered off, and the filtrate is evaporated to dryness. The residue is dissolved in dry DMF, and pyridine containing 6 to 8 equivalents of hydrochloric acid is added to the solution. The solvent is distilled off; the oily residue is triturated with water, the solids are filtered off, washed with water and ethyl acetate, and dried. 3.22 g. (86.1 %) of H-25-39-OtBu.HCl are obtained. M.p.: 187°C (under decomposition), $R_f^{13}$ = 0.3.

Step 12:
Z-Lys(BOC)-Lys(BOC)-Arg(NO₂)-Arg(NO₂)-Pro-Val-Lys(BOC)-Val-Tyr(tBu)-Pro-Asn-Gly-Ala-Glu(OtBu)-Asp(OtBu)-Glu(OtBu)-Ser-Ala-Glu(OtBu)-Ala-Phe-Pro-Leu-Glu(OtBu)-Phe-OtBu Z-15-39-OtBu)

3.0 g. (1.5 mmoles) of H-25-39-OtBu.HCl and 3.1 g. (1.65 mmoles) of Z-Lys(BOC)-Lys(BOC)-Arg(NO₂)-Arg(NO₂)-Pro-Val-Lys(BOC)-Val-Tyr(tBu)-Pro-OH (see Brit. Pat. No. 1 201 053) are dissolved in 20 ml. of dry DMF. The solution is cooled to 0°C, and 0.166 ml. (1.5 mmoles) of N-methyl-morpholine are added to it, followed by 1.4 g. of DCC-PFPOH complex. The reaction mixture is stirred at room temperature for 24 hours; thereafter it is filtered into 400 ml. of ether. The separated precipitate is filtered off, suspended in acetone, stirred, and filtered again. 5.15 g. (90 %) of Z-15-39-OtBu are obtained. M.p.: 220°C (under decomposition); $R_f^{12}$ = 0.2; $R_f^6$ = 0.65.

Step 13:
H-Lys(BOC)-Lys(BOC)-Arg-Arg-Pro-Val-Lys(BOC)-Val-Tyr(tBu)-Pro-Asn-Gly-Ala-Glu(OtBu)-Asp(OtBu)-Glu(OtBu)-Ser-Ala-Glu(OtBu)-Ala-Phe-Pro-Leu-Glu(OtBu)-Phe-OtBu.3HCl (H-15-39-OtBu,3HCl)

5.0 g. (1.31 mmoles) of Z-15-39-OtBu are dissolved in 100 ml. of 80 % acetic acid. 3 g. of activated zinc powder are added to the solution, and the obtained suspension is stirred at room temperature. The progress of the reduction is monitored by thin layer chromatography. At the end of the reduction the suspension is filtered, the filtrate is evaporated, the residue is triturated with water, and the solids are filtered off. The product is dissolved in 300 ml. of 80 % acetic acid, and the mixture is hydrogenated in the presence of palladium-on-carbon. At the end of the reaction the catalyst is filtered off; the solution is evaporated to dryness, and the residue is triturated with ether. The solids are filtered off, dissolved in 40 ml. of pyridine, and 10 ml. of pyridine containing 1.5 ml. of concentrated hydrochloric acid are added to the solution under cooling. The obtained solution is evaporated, the residue is triturated with water, the solids are filtered off and washed with water. 4.0 g. (85 %) of H-15-39-OtBu-3HCl are obtained. M.p.: 208°C (under decomposition), $R_f^7$ = 0.35.

Step 14:
H-Ser-Tyr-Ser-Met-Glu-His-Phe-Arg-Trp-Gly-Lys-Pro-Val-Gly-Lys-Lys-Arg-Arg-Pro-Val-Lys-Val-Tyr-Pro-Asn-Gly-Ala-Glu-Asp-Glu-Ser-Ala-Glu-Ala-Phe-Pro-Leu-Glu-Phe-OH (H-1-39-OH)

3.6 g. (1.0 mmole) of H-15-39-OtBu-3HCl and 2.0 g. (1 mmole) of BOC-Ser-Tyr-Ser-Met-Glu(OtBu)-His-Phe-Arg-Trp-Gly-Lys(BOC)-Pro-Val-Gly-OH.HCl (see Brit. Pat. No. 1 201 053) are dissolved in 20 ml. of DMF. The solution is cooled to 0°C, and 0.11 ml. (1 mmole) of N-methyl-morpholine and 0.95 g. of DCC-PFPOH complex are added to it. The reaction mixture is stirred at room temperature for 24 hours, thereafter it is filtered into 200 ml. of ether. The separated product (5.6 g. $R_f^7$ = 0.55) is filtered off, and washed with ether and water.

1 g. of the above compound is dissolved in the mixture of 20 ml. of trifluoroacetic acid and 1 ml. of mercaptoethanol. The solution is left to stand at room temperature for one hour, thereafter it is evaporated in vacuo. The residue is dissolved in 20 ml. of water, and the obtained solution is evaporated again in vacuo. The residue is dissolved in 10 ml. of water, and the trifluoroacetate ions are replaced for acetate ions using an Amberlite IRA 410 ion exchanger (acetate form). The obtained solution is freeze-dried, and the crude product is purified using a column of CM-32 ion exchanger. As eluting agents, 0.13 molar (pH = 6.6) and 0.25 molar (pH = 7) ammonium acetate solutions are used. The fractions containing the aimed product are combined and freeze-dried. 0.6 g. (60 %) of H-1-39-OH are obtained. $R_f^{14}$ = 0.25.

Amino acid analysis: Asp 1.9 (2); Ser 2.7 (3); Glu 4.7 (5); Pro 3.8 (4); Gly 3.0 (3); Ala 3.0 (3); Leu 1.0 (1); Val 2.9 (3); Met 0.95 (1); Tyr 1.9 (2); Phe 3.0 (3); His 0.95 (1); Lys 3.8 (4); Arg 2.8 (3); Tyr:Trp = 2.1 (2.0)

What we claim is:
1. A process for the preparation of a peptide having the formula (I)

Ser-Tyr-Ser-Met-Glu-His-Phe-Arg-Trp-Gly-Lys-
Pro-Val-Gly-Lys-Lys-Arg-Arg-Pro-Val-Lys-Val-
Tyr-Pro-Asn-Gly-Ala-Glu-Asp-Glu-Q wherein Q is selected from the group which consists of:
a. Ser-OH,
b. Ser-Ala-OH,
c. Ser-Ala-Glu-OH,
d. Ser-Ala-Glu-Ala-OH,
e. Ser-Ala-Glu-Ala-Phe-OH,
f. Ser-Ala-Glu-Ala-Phe-Pro-OH,
g. Ser-Ala-Glu-Ala-Phe-Pro-Leu-OH,
h. Ser-Ala-Glu-Ala-Phe-Pro-Leu-Glu-OH, or i. Ser-Ala-Glu-Ala-Phe-Pro-Leu-Glu-Phe-OH,
which comprises the step of:
  A. reacting a first peptide of the formula
    BOC-Ser-Tyr-Ser-Met-Glu(OtBu)-His-Phe-Arg-
    Trp-Gly-Lys(BOC)-Pro-Val-Gly-OH
  with a second polypeptide of the formula
    -Lys(BOC)-Lys(BOC)-Arg-Arg-Pro-Val-Lys(BOC)-
    Val-Tyr(tBu)-Pro-Asn-Gly-Ala-Glu(OtBu)-
    Asp(OtBu)-Glu(OtBu)-O, the latter Q moiety having blocked Glu and C-terminal amino acid units, in equimolar amount with the first polypeptide and in the presence of excess pentafluorophenol and dicyclohexyl carbodimide at a temperature of about 0°C.

* * * * *